(12) United States Patent    (10) Patent No.:     US 8,195,268 B2
Lin et al.                    (45) Date of Patent:     Jun. 5, 2012

(54) HIGH-DENSITY MICRO ELECTRODE ARRAY AND SERIAL CONTROL METHOD THEREOF

(75) Inventors: Chii-Wann Lin, Taipei (TW);
Jyh-Horng Chen, Taipei (TW);
Feng-Chi Yang, Taipei (TW)

(73) Assignee: National Taiwan University, Taipei (TW)

( * ) Notice: Subject to any disclaimer, the term of this patent is extended or adjusted under 35 U.S.C. 154(b) by 544 days.

(21) Appl. No.: 12/393,964

(22) Filed: Feb. 26, 2009

(65) Prior Publication Data
US 2010/0145179 A1    Jun. 10, 2010

(30) Foreign Application Priority Data
Dec. 5, 2008 (TW) .............................. 97147521 A

(51) Int. Cl.
*A61B 5/04* (2006.01)
*A61N 1/00* (2006.01)
(52) U.S. Cl. ......... 600/378; 600/377; 600/544; 607/116
(58) Field of Classification Search .................. 600/373, 600/377–378, 393, 544–547; 607/116
See application file for complete search history.

(56) References Cited

U.S. PATENT DOCUMENTS

| | | | | |
|---|---|---|---|---|
| 5,388,577 A * | 2/1995 | Hubbard | ........................ | 600/377 |
| 5,810,725 A * | 9/1998 | Sugihara et al. | ............... | 600/372 |
| 6,038,477 A * | 3/2000 | Kayyali | ........................ | 607/72 |
| 6,330,466 B1 * | 12/2001 | Hofmann et al. | ............. | 600/378 |
| 7,911,238 B2 * | 3/2011 | Lin et al. | ........................ | 327/99 |
| 2010/0106041 A1 * | 4/2010 | Ghovanloo et al. | ........... | 600/544 |

OTHER PUBLICATIONS

Richard Norman, Principles of Bioinstrumentation, May 10, 1988, John Wiley & Sons, pp. 390-391.*

* cited by examiner

*Primary Examiner* — Linda Dvorak
*Assistant Examiner* — Brian M Antiskay
(74) *Attorney, Agent, or Firm* — WPAT, P.C.; Anthony King

(57) ABSTRACT

Each micro electrode of a high-density micro electrode array is connected to the same conducting wire. Serial switches enable sequential electrical connection of the micro electrode array. Given reasonable temporal resolution, the separation interval of two consecutive instances of the same micro electrode entering the ON state matches the temporal resolution. The micro electrode array has simple layout and small area, thereby maximizing the number of micro electrodes installed per unit area.

8 Claims, 8 Drawing Sheets

HIGH-DENSITY MICRO ELECTRODE ARRAY AND SERIAL CONTROL METHOD THEREOF

BACKGROUND OF THE INVENTION

1. Field of the Invention

The present invention relates to a micro electrode array for measuring bioelectric signals and a method for controlling the same, and more particularly to a high-density micro electrode array and a serial control method thereof.

2. Description of the Prior Art

Owing to advancement of biomedical measurement technology, micro electrodes can help to miniaturize a detector and downsize it, decrease detector power consumption, therefore, they are fit for mass production. The detector has plenty of miniaturized electrode elements, and thus it is feasible to build a micro electrode array measuring platform for measuring a plurality of physiological parameters concurrently.

Referring to FIG. 1, a conventional electrode element 100, basically, comprises an electrode point 101 and a conducting wire 103. The electrode point 101 is the exposed metal portion of the electrode point 101. The electrode point 101 is used in contact with a measurement portion, and it allows the electrode element to receive a signal by a related mechanism, namely electrode-electrolyte interface. Afterward, the signal is sent to a back end via the conducting wire 103 for further processing. The conducting wire 103 is required to be insulated very well so as to ensure the effective delivery of the signal. Given its aforesaid basic structure, the electrode element can measure signals in real time so as to maintain high temporal resolution.

Owing to the presence of the basic structures in a micro electrode array, the basic structures must be insulated from each other in order to prevent crosstalk between different signals. To ensure high yield of a detection chip, the distance between any two basic structures (including the electrode point and the conducting wire) has to be the minimum space set forth in the design rule of a fabrication process so as to enable smooth transmission of signals by the conducting wire to a back end for further processing. However, the space limitation affects spatial resolution.

Both temporal resolution and spatial resolution are important to related application of a micro electrode array. Take recording neural signal network, for example, it requires its spatial resolution to be one or two neurons in order to evaluate the route whereby neural electrophysiological signals are transmitted. Regarding application of electrical stimulation, appropriate spatial resolution can ensure precise electrical stimulation at one or more points, but prevents unnecessary portions to be electrical stimulated. Take human interface for example, high precision of signal resolution is required.

FIG. 2 shows a schematic view of conventional layout of electrodes in one dimension, the electrode point 101 has to be connected to the conducting wire 103 so as to transmit an electrical signal. Regarding a conventional electrode array, the electrode points have positive correlation with the conducting wires in quantity, primarily because each of the electrode points has to be connected to a conducting wire. Hence, the number of the electrode points deployed is limited by the area of a substrate 201. On the other hand, spatial resolution of a micro electrode array depends on the number of the electrode points. Therefore, the layout of a conventional micro electrode array is a hindrance to the optimization of spatial resolution.

On the other hand, some detection chips have to penetrate biological tissue, and the cross-section of the path of penetration (an electrode structure of one dimension) should be small so as to minimize any injury done to the biological subject. However, given a conventional layout, increasing spatial resolution definitely conflicts with the reduction of the cross-section of the path of penetration into biological tissue. Hence, to implement a conventional high-density micro electrode array, a large cross-section of the path of penetration into biological tissue is inevitable.

A conventional micro electrode array is disclosed in U.S. Pat. No. 5,388,577, entitled Electrode Array Microchip, and, another conventional micro electrode array is taught in Taiwanese Patent Publication No. 200628797, entitled Multiple-Channel Micro Electrode Probe and Method for Fabricating the Same", wherein the conventional micro electrode arrays comprise similar basic structure as described above. Although, the conventional micro electrode array has an advantage of real-time measurement. However, the conventional layout, which features a conducting wire and an electrode, brings a new problem, namely low spatial resolution in the presence of a limited cross-sectional area of a detection chip.

Therefore, the structure of a conventional micro electrode array, coupled with design rules, limits the spatial resolution of the micro electrode array greatly and, more particularly, puts implanted elements (penetration described above) at disadvantageous position because they are desirably downsized, but their spatial resolution is unlikely to increase.

SUMMARY OF THE INVENTION

It is an objective of the present invention to provide a high-density micro electrode array for enhancing spatial resolution, enhancing spatial resolution of the micro electrode array at the cost of the advantage of real-time measurement and on condition that temporal resolution is reasonable, and streamlining the circuitry, so as to minimize the total surface area covered by the circuitry on a substrate and reduce signal loss.

To achieve the above and other objectives, the present invention discloses a high-density micro electrode array, comprising a plurality of micro electrodes connected to a main conducting wire, thereby allowing an electrical signal measured to be transmitted by each of the micro electrodes via the conducting wire; a plurality of switch units corresponding in position to the micro electrodes, the switch units each being connected between the conducting wire and each of the micro electrodes so as to control an ON state and an OFF state of the conducting wire-based signal transmission; and a substrate for carrying the micro electrodes, the conducting wire, and the switch units so as to form a high-density micro electrode array.

To allow the micro electrodes to enter an ON state sequentially according to the present invention, the switch units enable each of the micro electrodes to be at an ON state for a first time interval before entry into an OFF state, and then the switch units enable the next one of the micro electrodes to be at an ON state, such that the separation interval between the first and second instances of the same micro electrode sending an electrical signal is defined as a second time interval. The first time interval is the quotient obtained when the least temporal resolution of the electrical signals is divided by the quantity of the micro electrodes. The second time interval equals the least temporal resolution.

Another objective of the present invention is to provide a serial control method for a high-density micro electrode array. The method comprises the steps of: providing a micro electrode array, the micro electrode array comprising a plurality of micro electrodes for generating an electrical signal; and providing a serial switch array connected to the micro electrode array, wherein a first time interval is defined as a time interval of an ON state of the micro electrodes, allowing a plurality of electrical signals generated by the micro electrodes to be sequentially sent to a recorder via a main conducting wire, and retrieving from the recorder one of the electrical signals measured by the same micro electrode so as to obtain a complete corresponding one of the electrical signals for each of the micro electrodes.

To enable the micro electrodes to enter an ON state sequentially, in a preferred embodiment of a serial control method of a high-density micro electrode array of the present invention, the first time interval is the quotient obtained when the least temporal resolution of the electrical signals is divided by the quantity of the micro electrodes. The separation interval of two consecutive instances of the same micro electrode entering an ON state equals the least temporal resolution.

DETAILED DESCRIPTION OF THE EMBODIMENT

The present invention is herein illustrated with preferred embodiments in conjunction with the accompanying drawings, so that one skilled in the pertinent art can easily understand other objectives, features, advantages and effects of the present invention from the disclosure of the invention.

Regarding a high-density micro electrode array with serial switches of the present invention, if the least temporal resolution of a signal to be measured by the micro electrode array is defined with T, a serial switch preceding each micro electrode enables the micro electrodes to enter an ON state sequentially, and the same micro electrode enters the ON state per every period of T. In other words, when the same micro electrode entering the ON state per each period is greater than T, the signal measured by the micro electrode will not reflect the actual condition of a subject (such as, variation of a neural signal). For instance, assuming a micro electrode array has a total of n micro electrodes, the period of an ON state of the switch preceding each of the micro electrodes will be T/n.

Figure 1:
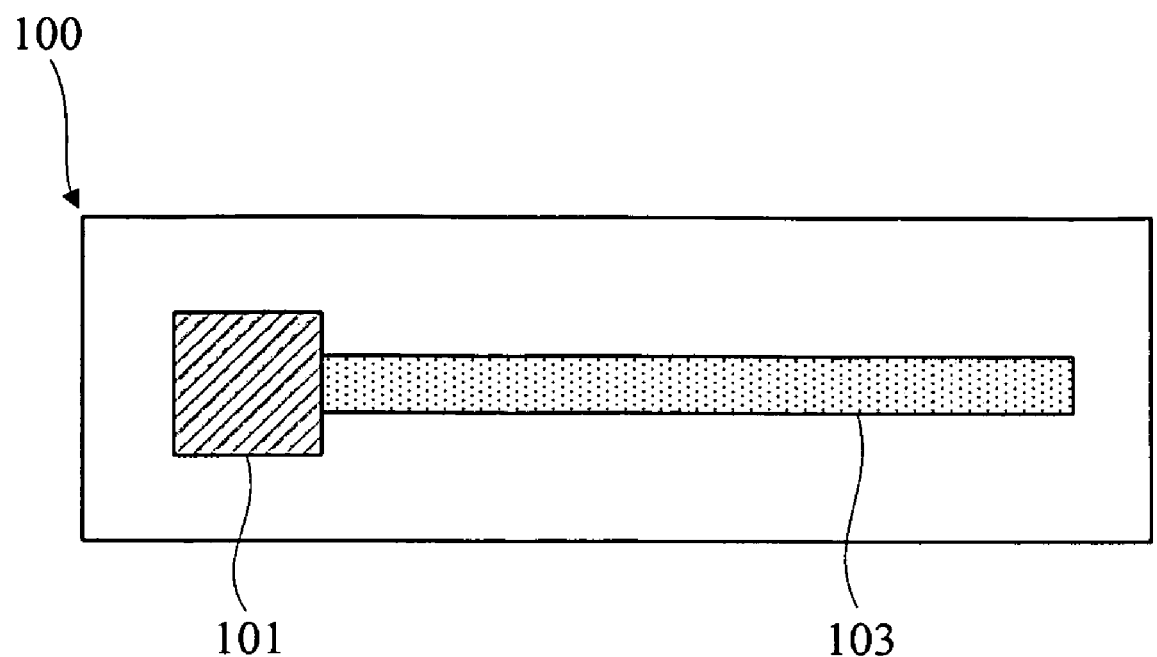
FIG. 1 is a schematic view of conventional basic electrode elements.
Figure 2:
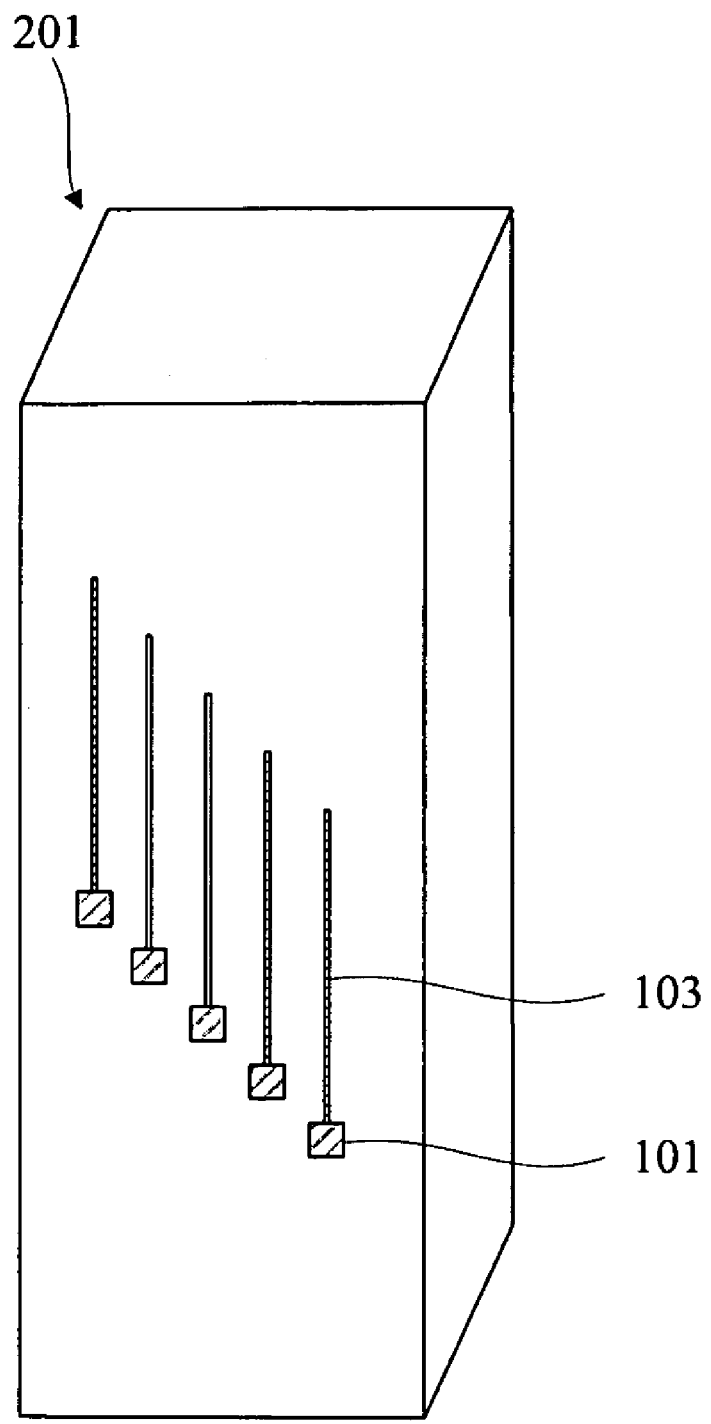
FIG. 2 is a schematic view of conventional layout of electrodes in one dimension.
Figure 3:
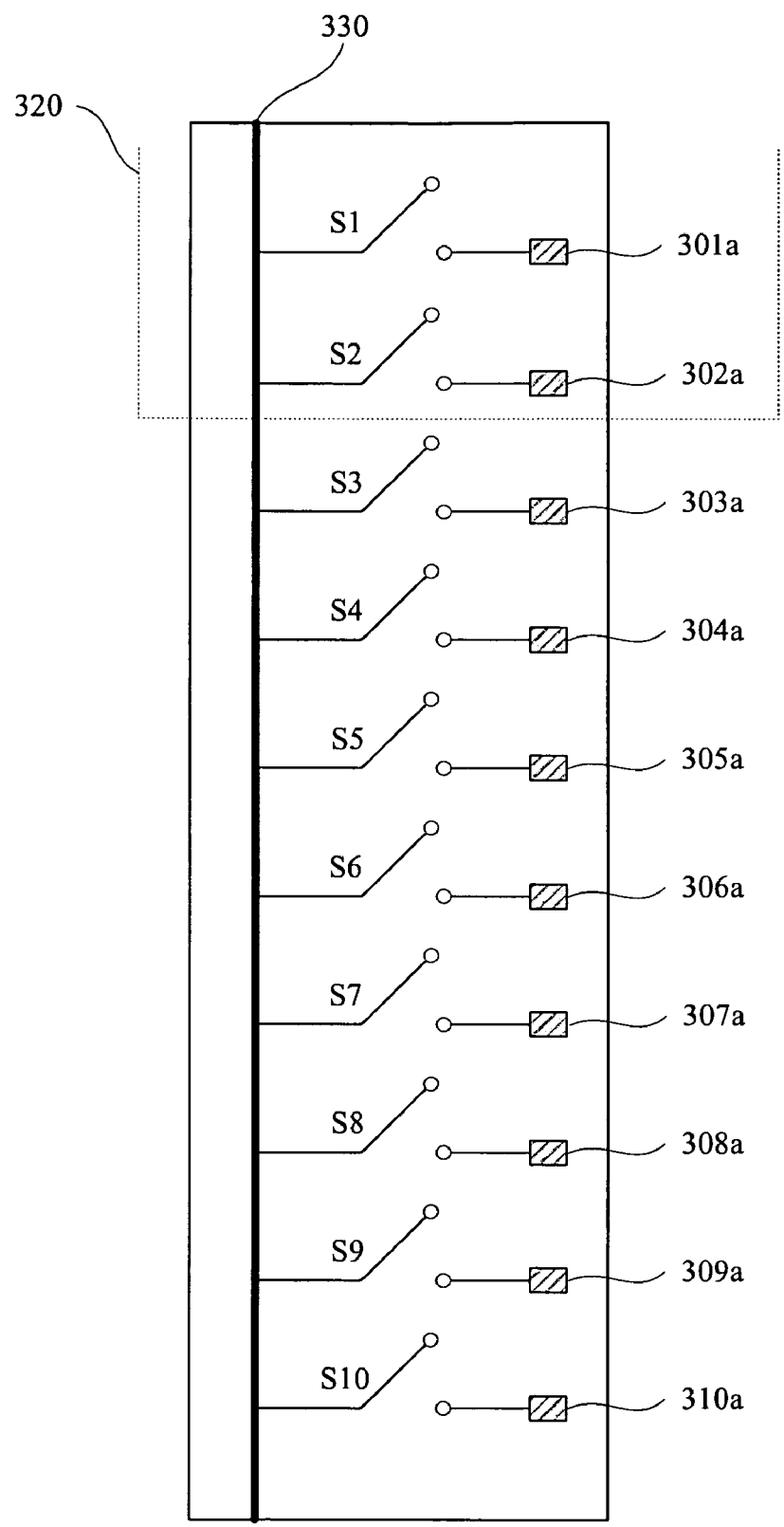
FIG. 3 is a schematic view of a circuit layout for serial switches and a micro electrode array thereof according to the present invention.

In a preferred embodiment of the present invention, a micro electrode array has a total of 10 micro electrodes. Referring to FIG. 3, which is a schematic view of a circuit layout for serial switches and a micro electrode array thereof according to the present invention. Switch units are denoted with S1 to S10, which are configured to control micro electrodes 301a to 310a, respectively, and are configured to determine whether a main conducting wire 330 is at an ON state. Referring to FIG. 3 again, a micro electrode is connected to a switch unit, and all the switch units are connected to the same conducting wire, thereby forming serial switches. Given the 10 switches, the ON state of each of the switch units has a time interval of T/10, or is known as the first time interval, as shown in Table 1 below.

TABLE 1

Table of the Time and Action of Switch Units Entering ON State in Sequence

| First Time Interval | ON/OFF |
| --- | --- |
| 0~T/10 | Q1 is ON, but others are OFF |
| T/10~2T/10 | Q2 is ON, but others are OFF |
| 2T/10~3T/10 | Q3 is ON, but others are OFF |
| 3T/10~4T/10 | Q4 is ON, but others are OFF |
| 4T/10~5T/10 | Q5 is ON, but others are OFF |
| 5T/10~6T/10 | Q6 is ON, but others are OFF |
| 6T/10~7T/10 | Q7 is ON, but others are OFF |
| 7T/10~8T/10 | Q8 is ON, but others are OFF |
| 8T/10~9T/10 | Q9 is ON, but others are OFF |
| 9T/10~T | Q10 is ON, but others are OFF |
| T~11T/10 | Q1 is ON, but others are OFF (repeated) |

As shown in Table 1, the time interval between the first and second instances of the same micro electrode entering an ON state is defined as a second time interval, and conforms to the least temporal resolution T.

Figure 4:
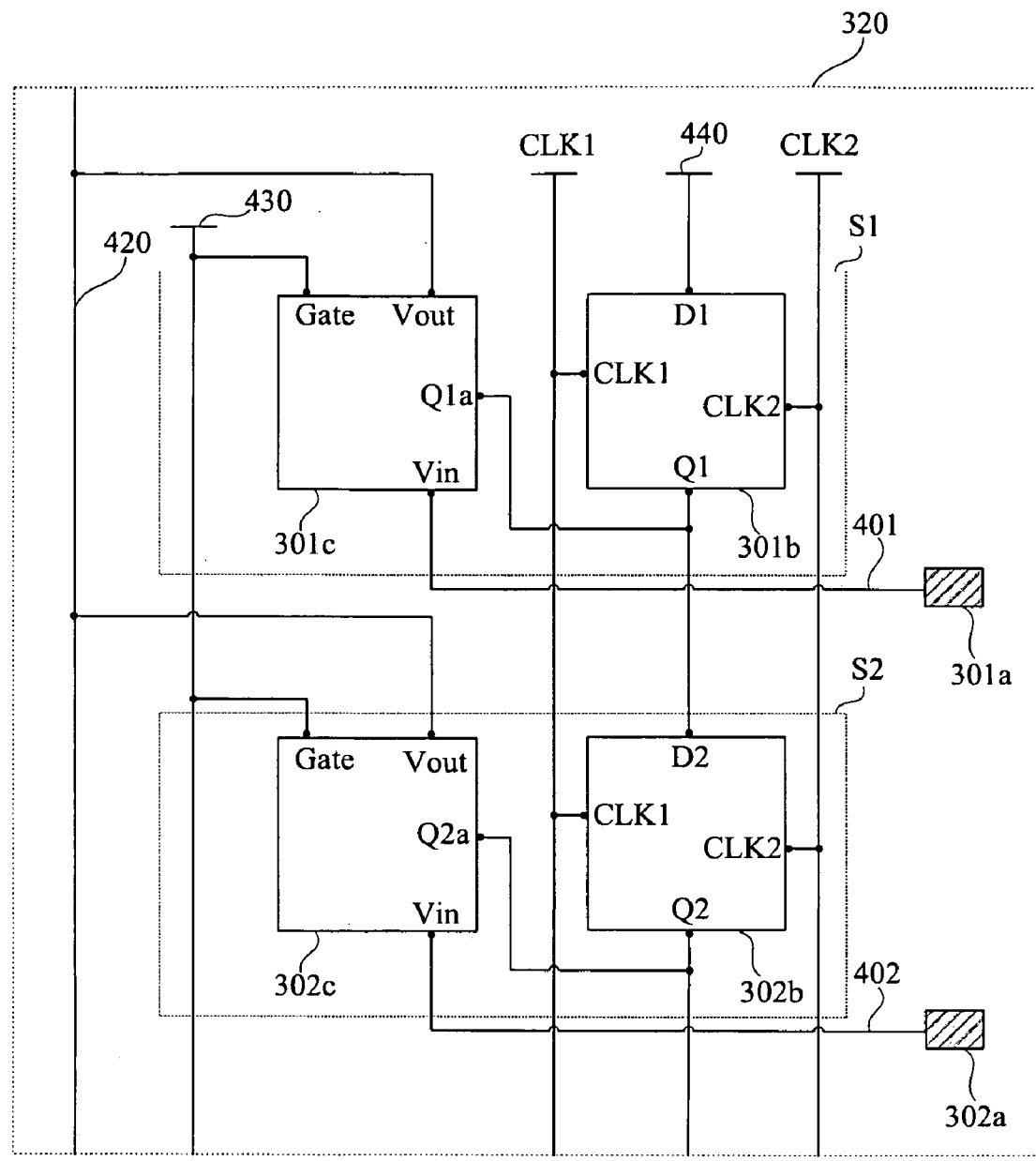
FIG. 4 is a circuit for switch units of the present invention.

Each of the switch units each comprises a switch circuit and a switch control circuit. The following description is illustrated with a region 320 of FIG. 3. Referring to FIG. 4, which is a circuit for switch units of the present invention and is illustrated with switch units S1 and S2, and switch unit S1 comprises a switch circuit 301c and a switch control circuit 301b and is connected to the micro electrode 301a corresponding in position thereto, and the switch unit S2 comprises a switch circuit 302c and a switch control circuit 302b and is connected to the micro electrode 302a corresponding in position thereto.

The switch control circuit controls sending an ON signal and an OFF signal. In case of the ON signal, the switch control circuits 301b, 302b send the ON signal from output ends Q1, Q2 to input ends Q1a, Q2a of the switch circuits 301c, 302c, respectively. In case of the OFF state, the switch control circuits 301b, 302b send the OFF signal from the output ends Q1, Q2 to the input ends Q1a, Q2a of the switch circuits 301c, 302c, respectively.

The switch circuit is formed from two complementary metal-oxide semiconductor (CMOS) circuits connected in series, namely a first sub-switch and a second sub-switch (not shown). Different signals control and determine whether the two sub-switches enter an ON state. The first sub-switch corresponds in position to the input ends Q1a, Q2a of the switch circuit, so as to receive the ON signal or the OFF signal from the output ends Q1, Q2 of the switch control circuit. The first sub-switch enters an ON state when it receives the ON signal. Conversely, the first sub-switch enters an OFF state when it receives the OFF signal. The second sub-switch corresponds in position to a gate of the switch circuit, and the gate receives a gate ON signal or a gate OFF signal from a gate signal source 430. The gate ON signal or the gate OFF signal is sent to all the switch circuits. Each of the switch circuits receives the same signal, that is, the same gate ON signal or the same gate OFF signal. The gate ON signal or the gate OFF signal from the gate signal source 430 also control and determine whether the second sub-switches are at an ON state or an OFF state.

Both the first sub-switch and the second sub-switch have to receive an ON signal before the switch units enter an ON state in whole. In other words, both the two sub-switches have to be at an ON state so as for an electrical signal measured by the micro electrodes to be sent to Vin of the switch circuit 301c, 302c via a conducting wire 401 or 402 (depending on whether the ON state is activated by the switch unit S1 or S2), and then the electrical signal is sent from Vout to a main conducting wire 330 before being delivered to a data recorder (not shown).

Figure 5:
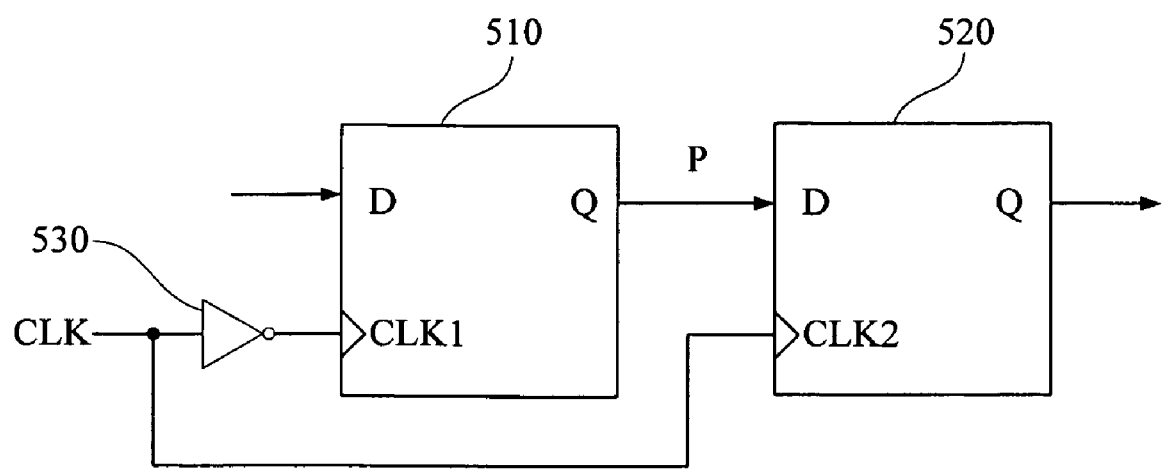
FIG. 5 is a schematic view of a logical circuit for master-slave flip-flops of a switch control circuit.

Referring to FIG. 5, which is a schematic view of a logical circuit for master-slave flip-flops of a switch control circuit, each switch control circuit is formed from two positive edge-triggered D-type flip-flops and an inverter 530 connected in series, and characterized by the D-type flip-flops in master-slave configuration. A clock CLK is sent, via the inverter 530, to a first D-type flip-flop 510 to become a first clock CLK1. Alternatively, a clock CLK is sent, without passing the inverter 530, to a second D-type flip-flop 520 to become a second clock CLK2. The first D-type flip-flop 510 has an input end D for receiving an input signal, and has an output end Q for sending a signal P. The second D-type flip-flop 520 also has an input end D for receiving the signal P, and an output end Q for sending the ON/OFF signal. Owing to the master-slave configuration, the first clock CLK1, the second clock CLK2, and the input signal together control the ON/OFF signal from each of the switch units S1-S10, which is to be described below in conjunction with the description of FIG. 6. Referring to FIG. 4, regarding the switch unit S1, a D end signal is sent from a D end signal output source 440 to an input end D1, and then an ON signal is sent from an output end Q1 to the input end Q1a; meanwhile, the ON signal sent from the output end Q1 also arrives at an input end D2 of the switch unit S2 to become an input signal.

In the preferred embodiment, which is exemplified by the least temporal resolution being equal to 1 µs, the time interval for an ON state of each of the switch units S1-S10 is equal to 1/10=0.1 µs and defined as the first time interval. In so doing, a separation interval between consecutive instances of an ON state of the same one of the switch units equals the least temporal resolution T, that is, the second time interval. Hence, it is necessary to configure a timing sequence of the first clock CLK1 and the second clock CLK2 so as to change the signal from the output end Q1-Q10 of each of the switch units every 0.1 µs. It is feasible to put each of the switch units S1-S10 at an ON state on a periodic basis so as to achieve the required temporal resolution, by controlling the period of the timing sequence of the D end signal sent from the D end signal output source 440.

Figure 6:
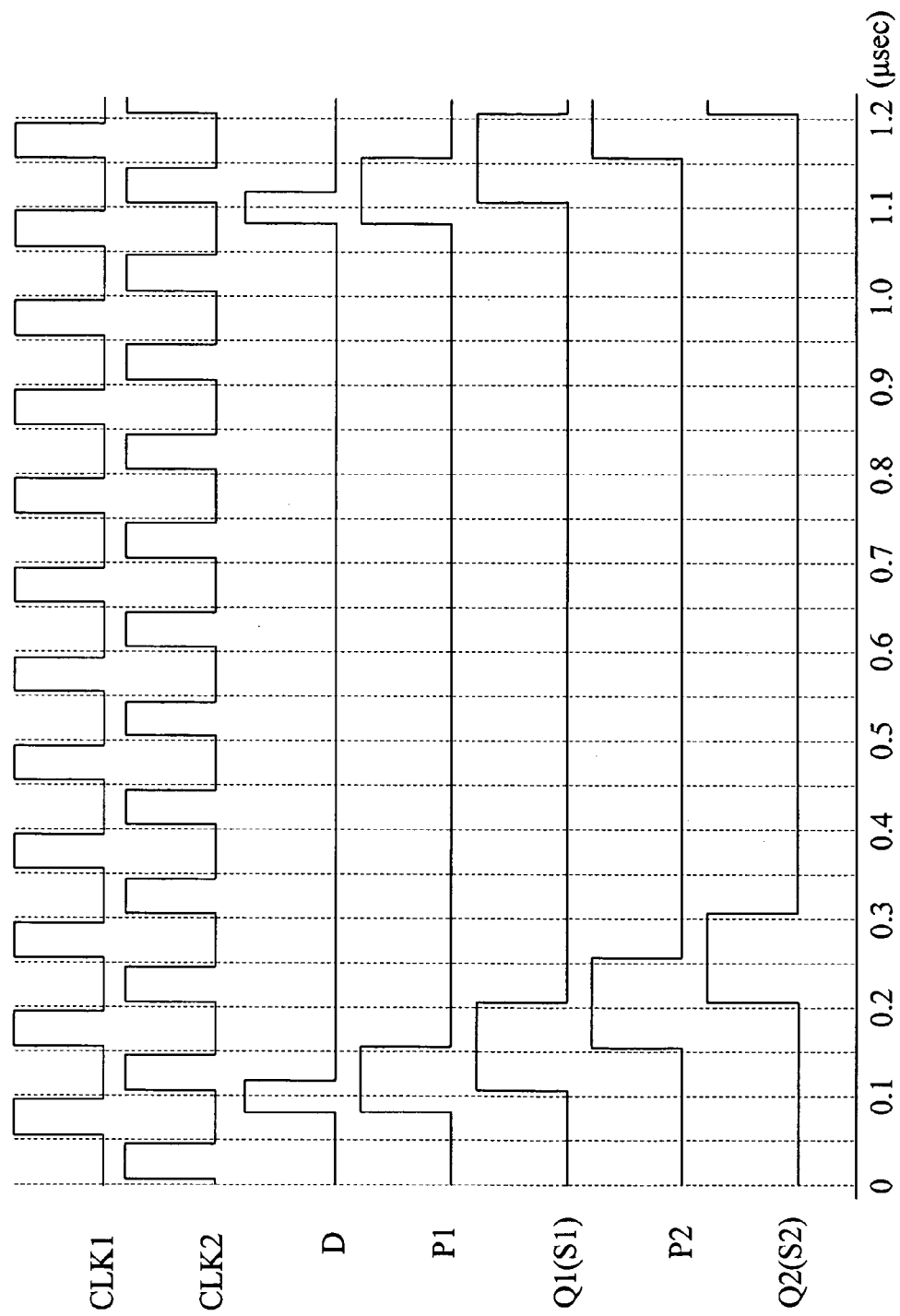
FIG. 6 is a timing sequence diagram of the master-slave flip-flops of the present invention.

Referring to FIG. 6, which is a timing sequence diagram of the master-slave flip-flops of the present invention and is illustrated with the first switch unit S1 and the second switch unit S2, the timing sequence of the first clock CLK1, the second clock CLK2, and the D end signal are configured, and the signals from the output ends Q1, Q2 change every 0.1 µs. As shown in the drawing, Q1(S1) and Q2(S2) express variation of the timing sequence. Q1(S1) expresses variation of the timing sequence at the output end Q1 of the switch unit S1, and Q2(S2) expresses variation of the timing sequence at the output end Q2 of the switch units S2.

Referring to FIG. 5 and FIG. 6 together, at 0.06-0.09 µs, the clock CLK is low level (i.e., CLK=0), and when the first clock CLK1 passes the inverter 530, it is at high level (i.e., CLK1=1); meanwhile, the first D-type flip-flop 510 is directly passed, and thus the signal P1 immediately follows the D end signal. However, at this moment, the second clock CLK2 which has not passed the inverter 530 is at low level (i.e., CLK2=0), and thus the second D-type flip-flop 520 maintains the existing signal level, that is, the low-level OFF signal from the output end Q1 (S1). At 0.09 µs, the first clock CLK1 is at low level (i.e., CLK1=0), and thus the first D-type flip-flop 510 turns OFF immediately, and the signal P1 remains the high-level signal that exists before the OFF state until the first clock CLK1 turns to high level (i.e., CLK1=1), and in consequence the signal P1 will turn to low level together with the D end signal only when the first D-type flip-flop 510 turns ON again (at 0.16 µs).

Variation of the second clock CLK2 is described below. At 0.11 µs, the second clock CLK2 turns to high level (i.e., CLK2=1), and thus the second D-type flip-flop 520 turns ON immediately, allowing the output signal from the output end Q1 (S1) to follow the signal P1. Hence, after 0.11 µs, the output end Q1 (S1) outputs a high level signal, that is, an ON signal. At 0.14 µs, the second clock CLK2 turns to low level (i.e., CLK2=0), and the second D-type flip-flop 520 immediately turns OFF. The output end Q1 (S1) maintains the high level signal that exists prior to the OFF state, that is, an ON signal, until the second clock CLK2 turns to high level (i.e., CLK2=2), and in consequence the output end Q1 (S1) will turn to low level, that is, an OFF signal, together with the signal P1 only when the second D-type flip-flop 520 turns ON again (i.e., at 0.21 µs).

Figure 7:
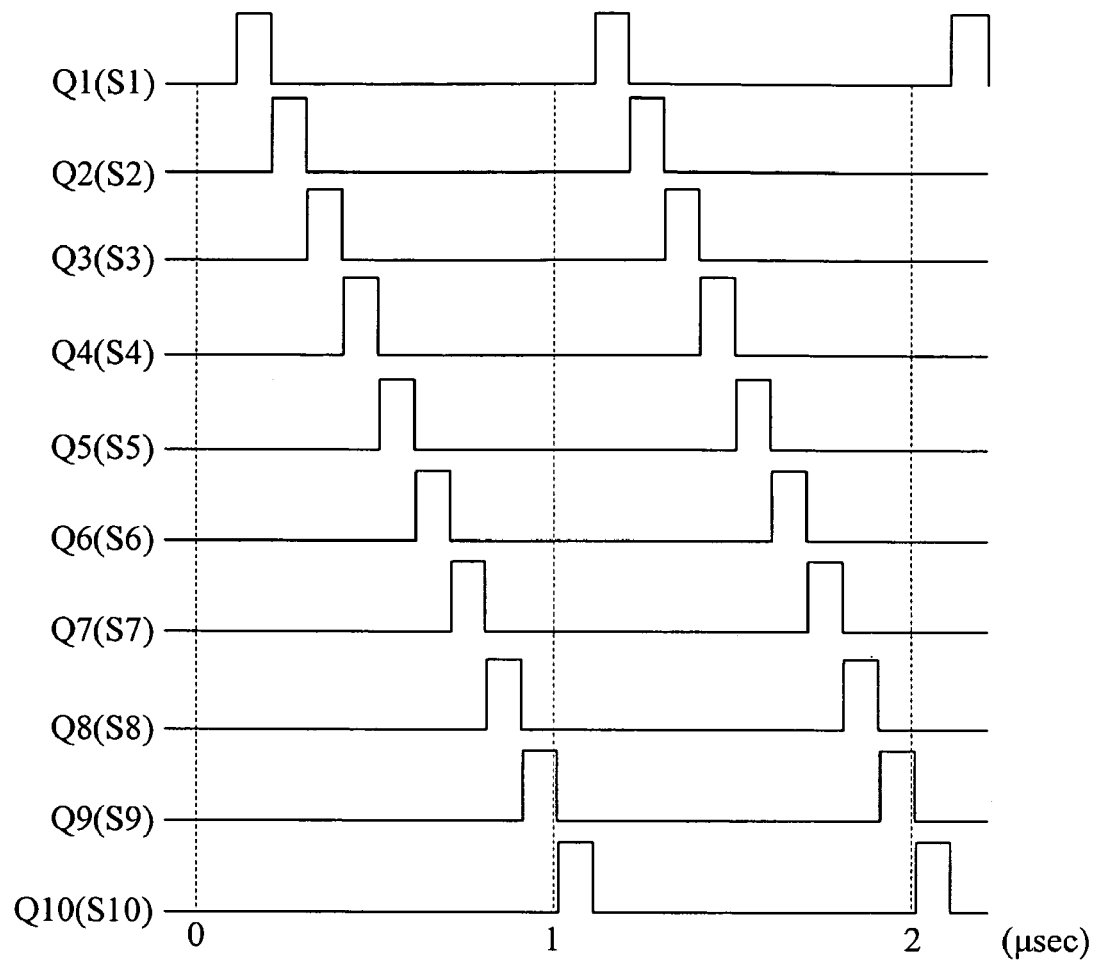
FIG. 7 is a diagram showing ON/OFF signals outputted from switches against time according to the present invention.

Afterward, a signal from the output end Q1 (S1) of the switch units S1 is treated as an input signal to the switch unit S2, and the above procedure repeats. The aforesaid cycle enables the switch units S1-S10 to enter an ON state on a periodic basis, and the time interval of an ON state is defined as the first time interval. In the preferred embodiment, the first time interval is equal to 0.1 µs. Referring to FIG. 7, which is a diagram showing ON/OFF signals outputted from switches against time according to the present invention, the switch units S1-S10 send out an ON signal sequentially, and the separation interval between two consecutive instances of an ON state of the same one of the switch units is equal to the least temporal resolution, that is, 1 µs. Hence, if the gate signal source 430 gives an instruction to send a gate ON signal, all the second sub-switches of the switch units S1-S10 will turn ON. In other words, all the switch units will be at an ON state, provided that all the first sub-switches of the switch units are ON, as an electrical signal measured by the micro electrodes corresponding in position to the switch units is sent from the micro electrodes. According to the present invention, the timing of the ON state of the first sub-switches are put under control, so as to enable the switch units to enter an ON state sequentially and allow a measured electrical signal to be equal to the least temporal resolution; hence, the waveforms and characteristics of the electrical signal can still be observed, and the measurement remains significant.

Figure 8:
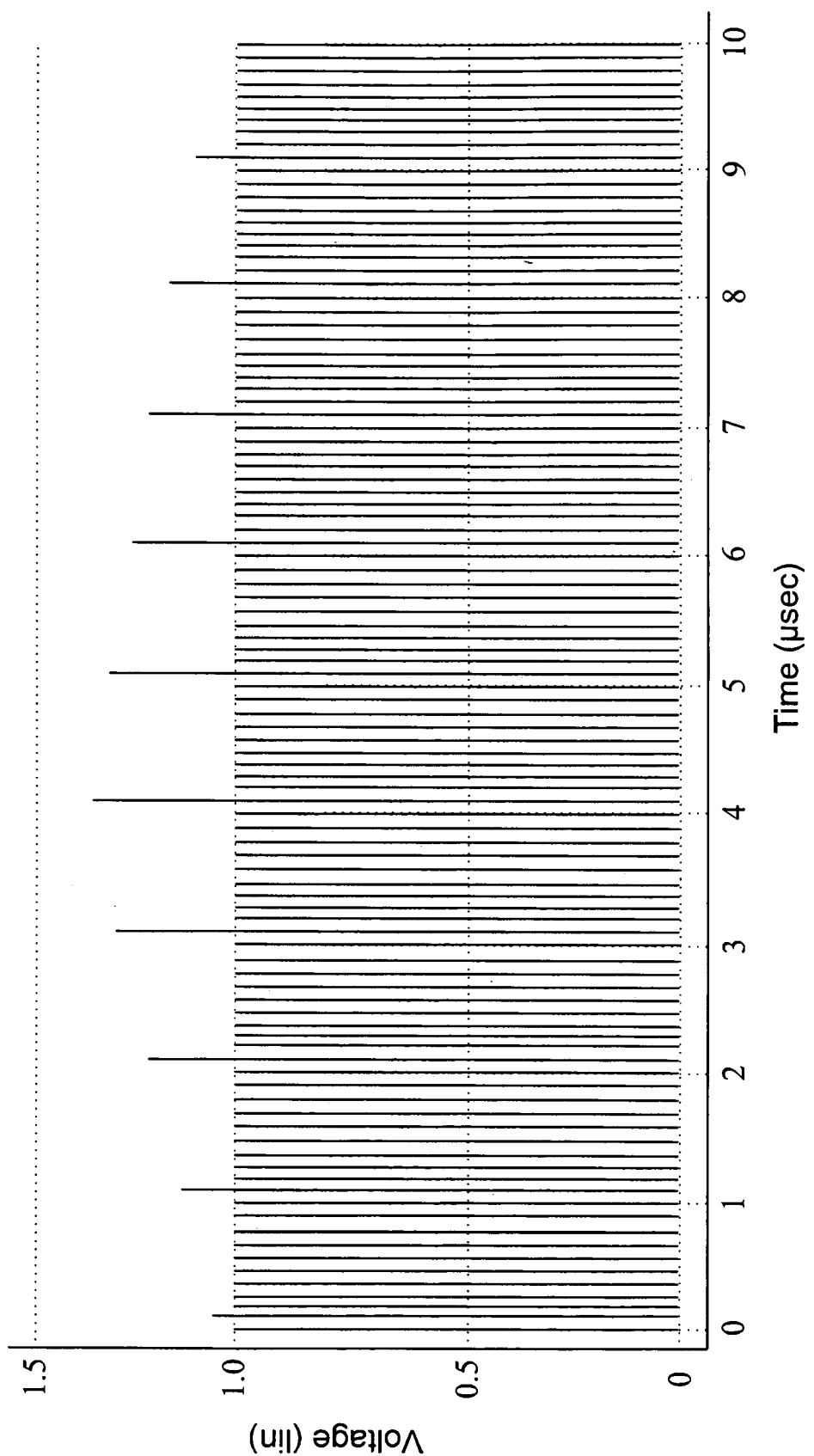
FIG. 8 is a schematic view of signals measured by the micro electrode array of the present invention.

Referring to FIG. 8, which is a schematic view of signals measured by the micro electrode array of the present invention, the horizontal axis represents time, and the vertical axis represents voltage measured by the micro electrodes. To better describe the present invention, the preferred embodiment discloses variation in an electrical signal measured by the micro electrode 301a corresponding in position to the switch unit S1, and discloses no variation in an electrical signal measured by remaining said micro electrodes 302a to 310a. As shown in the drawing, all the electrical signals measured at 0.1-0.2, 1.1-1.2, 2.1-2.2, 3.1-3.2, 4.1-4.2, 5.1-5.2, 6.1-6.2, 7.1-7.2, 8.1-8.2, and 9.1-9.2 µs are measured by the micro electrode 301a. Hence, electrical signals measured by same said micro electrodes are retrieved so as to be resolved to become electrical signals measured by corresponding one of the micro electrodes.

In short, the present invention provides a high-density micro electrode array having serial switches, allows each of the micro electrodes to be connected to the same conducting wire, enables the micro electrodes to enter an ON state sequentially by means of the serial switches, and allows a separation interval between two consecutive instances of an ON state of the same one of the micro electrode to match the temporal resolution of the micro electrode array at the cost of the advantage of real-time measurement and on condition that temporal resolution is reasonable, thereby streamlining the circuit layout of the micro electrode array, reducing the surface area of the micro electrode array, and maximizing the number of micro electrodes installed per unit area.

The foregoing specific embodiment is only illustrative of the features and functions of the present invention but is not intended to restrict the scope of the present invention. It is apparent to those skilled in the art that all equivalent modifications and replacement made in the foregoing embodiment according to the spirit and principle in the disclosure of the present invention should fall within the scope of the present invention. Hence, the scope of the present invention should be defined with the claims appended.

What is claimed is:

1. A high-density micro electrode array positioned on a substrate of a sensing portion of a sensor, comprising:
   a plurality of micro electrodes arranged in series on the substrate of the sensing portion of the sensor and connected to a single main conducting wire on the substrate of the sensing portion of the sensor, wherein electrical signals measured by the micro electrodes respectively, are transmitted via the main conducting wire; and
   a plurality of switch units positioned on the substrate of the sensing portion of the sensor, arranged in series with the micro electrodes, and each connected in between the main conducting wire and a corresponding one of the micro electrodes in order to control an ON state and an OFF state of transmission paths between the main conducting wire and the micro electrodes, wherein, under control of the switch units, the micro electrodes one by one enter the ON state and after a first time interval therefrom switch to the OFF state, the first time interval being determined by dividing a least temporal resolution of the electrical signals by a quantity of the micro electrodes, wherein the electrical signals leave the same micro electrode one by one at a second time interval.

2. The high-density micro electrode array of claim 1, wherein every switch unit comprises a switch circuit and a switch control circuit.

3. The high-density micro electrode array of claim 2, wherein the switch control circuit comprises D-type flip-flops in master-slave configuration.

4. The high-density micro electrode array of claim 2, wherein the switch circuit comprises a first sub-switch, the first sub-switch enters into the ON state when it receives an ON signal from the switch control circuit, and enters into the OFF state when it receives an OFF signal from the switch control circuit.

5. The high-density micro electrode array of claim 4, wherein the switch circuit further comprises a second sub-switch, the second sub-switch enters into the ON state when it receives a gate ON signal from a gate signal source, and enters into the OFF state when it receives a gate OFF signal from the gate signal source.

6. The high-density micro electrode array of claim 5, wherein the switch units enter the ON state when the first sub-switch and the second sub-switch are at the ON state so that the transmission paths between the micro electrodes to the main conducting wire are at the ON state to transmit a measured electrical signal.

7. The high-density micro electrode array of claim 6, wherein the first sub-switch and the second sub-switch comprise complementary metal-oxide semiconductor (CMOS).

8. The high-density micro electrode array of claim 1, wherein the second time interval equals the least temporal resolution.

* * * * *